US00PP32604P2

(12) United States Plant Patent
Griffin

(10) Patent No.: US PP32,604 P2
(45) Date of Patent: Dec. 8, 2020

(54) ***ALOE* PLANT 'PURPLE HAZE'**

(50) Latin Name: *Aloe hybrid*
Varietal Denomination: PURPLE HAZE

(71) Applicant: Altman Specialty Plants, Inc, Vista, CA (US)

(72) Inventor: Kelly Griffin, Carlsbad, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 0 days.

(21) Appl. No.: 16/873,348

(22) Filed: Mar. 24, 2020

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Cassandra Bright

(57) ABSTRACT

A new and distinct cultivar of *Aloe* plant named 'PURPLE HAZE' is disclosed, characterized by upright growth habit, lavender-colored leaves with pink margins, and red flowers. The new variety is an *Aloe*, typically produced as a garden or container plant.

1 Drawing Sheet

Latin name of the genus and species: *Aloe* hybrid.
Variety denomination: 'PURPLE HAZE'.

BACKGROUND OF THE INVENTION

The new cultivar is a product of a planned breeding program. The seed parent is the unpatented *Aloe* 'Icycle II'. The pollen parent is the unpatented *Aloe parvula* x *Aloe* 'Viper'. The crossing was made in December 2017 at a commercial greenhouse in Vista, Calif. 'PURPLE HAZE' was found and selected by the inventor in January 2018 at the same greenhouse in Vista, Calif.

Asexual reproduction of the new cultivar 'PURPLE HAZE' was first performed by tissue culture at a commercial laboratory in Vista, Calif. in February 2018. 'PURPLE HAZE' has since produced several generations and has shown that the unique features of this cultivar are stable and reproduced true to type.

SUMMARY OF THE INVENTION

The cultivar 'PURPLE HAZE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PURPLE HAZE.' These characteristics in combination distinguish 'PURPLE HAZE' as a new and distinct *Aloe* cultivar:

1. Upright growth habit.
2. Lavender colored leaves with bright pink edges.
3. Red flowers.
4. Table top size *Aloe*, maturing at 6" across.

PARENTAL COMPARISON

Plants of the new cultivar 'PURPLE HAZE' are similar to the seed parent in most horticultural characteristics. However, plants of the new variety differ from the seed parent in the following:

1. The new variety produces more compact, upright rosettes than the seed parent.
2. The new variety has smoother leaf edges than the seed parent.
3. The new variety has a frosted appearance to the leaf blade from a glaucous layer not found on the seed parent.

Plants of the new cultivar 'PURPLE HAZE' are similar to the pollen parent in most horticultural characteristics. However, plants of the new variety differ in the following:

1. The new variety has a different plant form, more uniformly star-shaped than the pollen parent.
2. The new variety has a frosted appearance to the leaf blade from a glaucous layer not found on the pollen parent.
3. The new variety produces more upright rosettes than the pollen parent.

COMMERCIAL COMPARISON

'PURPLE HAZE' can be compared to the unpatented commercial variety *Aloe* 'White Lightning'. The two *Aloe* varieties are similar in most horticultural characteristics; however, the new variety differs in the following:

1. Plants of the new variety are larger and more open than plants of this comparator.
2. The new variety has more sandpaper- textured leaves than this comparator.
3. The new variety has a cleaner growth habit with better symmetry than does this comparator.

BRIEF DESCRIPTION OF THE PHOTOGRAPHS

The accompanying photograph illustrates in full color a typical plant of 'PURPLE HAZE' grown in a greenhouse in Vista, Calif. This plant is approximately 24 months old, shown in a 1 gallon container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2007 edition, except where general terms of ordinary dictionary significance are used. The following observations and measurements describe 'PURPLE HAZE' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'PURPLE HAZE.'

Age of the plant described: 2 years.

PROPAGATION

Time to initiate roots: Approximately 25 days at 22° C.

Root description: Fibrous. Brown, not accurately measured with the RHS chart.

Propagation method: Tissue culture.

PLANT

Growth habit: Upright rosette, offsetting to form clumps with time.

Container size: 6 inches.

Height: Approximately 18 cm to top of highest leaf. Approximately 45 cm to top of highest inflorescence.

Plant spread: Approximately 20 cm.

Growth rate: Moderate.

Branching characteristics: Offsetting from base.

FOLIAGE

Leaf:

*Arrangement.*—Rosette.

*Average length.*—Average 16-18 cm.

*Average width.*—Average 3-4 cm.

*Shape of blade.*—Lanceolate.

*Apex.*—Acuminate.

*Base.*—Clasping.

*Margin.*—Fringed, pink-colored edge.

*Texture of top surface.*—Specks and spines.

*Texture of bottom surface.*—Prickly.

*Quantity of leaves per plant.*—Average 10.

*Color.*—Young foliage upper side: Near RHS Greyed-Purple N187B, margin near Red 43C. Young foliage under side: Near RHS Greyed-Purple N187B, margin near Red 43D. Mature foliage upper side: Near RHS Greyed-Purple N187B, margin near Red 43C. Mature foliage under side: Near RHS Greyed-Purple N187B, margin near Red 43D.

*Venation.*—Linear. Color: Indistinguishable from leaf blade.

FLOWER

Natural flowering season: Rebloomer, three to four times a year.

Inflorescence type and habit: Panicle, seldom branched.

Rate of flower opening: Moderate, successive.

Flower longevity on plant: 1.5 months.

Quantity of flowers: 10 to 20.

Total inflorescence size:

*Height.*—Approximately 28 cm.

*Width.*—Approximately 8 cm.

Corolla:

*Arrangement.*—Perianth cylindrical/corolla small and reflexed.

*Length.*—Approximately 2.5 cm.

*Width.*—Approximately 1 cm at widest point.

*Color.*—Tepals: When opening: Outer surface: Near RHS Red 41A. Inner surface: Near RHS Yellow 10D. Fully opened: Outer surface: Near RHS Red 41B. Inner surface: Near RHS Yellow 10D.

Bud:

*Shape.*—Cylindrical.

*Length.*—Approximately 2.5 cm.

*Diameter.*—Approximately 0.5 cm.

*Color.*—Near RHS Red 41A.

Pedicels:

*Length.*—Approximately 1 cm.

*Width.*—0.02 cm.

*Aspect.*—Lateral.

*Color.*—Near RHS Red 42D.

Fragrance: None.

REPRODUCTIVE ORGANS

Stamens:

*Number.*—6.

*Filament length.*—Approximately 2.5 cm.

*Filament color.*—Near White N155A.

*Anther length.*—0.25 cm.

*Anther color.*—Near Yellow 8A.

*Anther shape.*—Oval.

*Pollen color.*—Near Yellow 13C.

Pistil:

*Number.*—1.

*Length.*—Approximately 3 cm.

*Style color.*—Near White N155A.

*Stigma.*—Shape: Rounded. Color: Near White N155A. Ovary color: Near RHS Green 139D.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C.

Disease/pest resistance: Shows mite resistance and black spot resistance.

What is claimed is:

1. A new and distinct cultivar of *Aloe* plant named 'PURPLE HAZE' as herein illustrated and described.

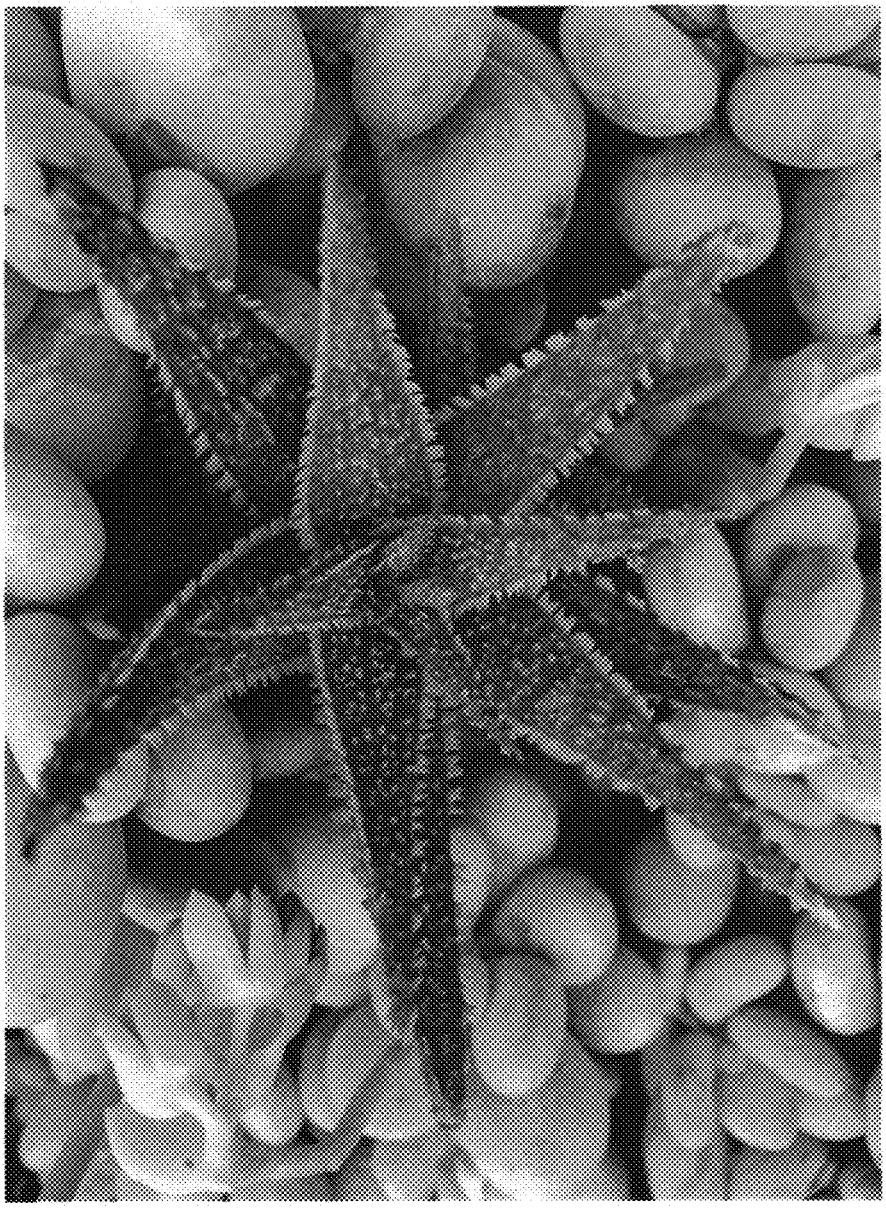

* * * * *